United States Patent

Early

Patent Number: 5,485,917
Date of Patent: Jan. 23, 1996

[54] QUICK RELEASE PACKAGE FOR SURGICAL INSTRUMENT

[75] Inventor: Timothy J. Early, Hamilton, Ohio

[73] Assignee: Ethicon-Endo-Surgery, Cincinnati, Ohio

[21] Appl. No.: 416,936

[22] Filed: Apr. 4, 1995

Related U.S. Application Data

[63] Continuation of Ser. No. 162,687, Dec. 6, 1993, abandoned.

[51] Int. Cl.$^6$ .................................................... B65D 73/00
[52] U.S. Cl. ............................................. 206/363; 206/471
[58] Field of Search ................................. 206/461, 462, 206/471, 363, 364, 499, 370; 221/305

[56] References Cited

U.S. PATENT DOCUMENTS

| | | | |
|---|---|---|---|
| 3,580,472 | 5/1971 | Stawski. | |
| 3,759,375 | 9/1973 | Nappi | 206/370 X |
| 3,872,966 | 3/1975 | Gordon et al. | 206/499 X |
| 4,005,776 | 2/1977 | Seeley | 206/461 X |
| 4,324,331 | 4/1982 | Ignasiak | 206/363 |
| 5,082,112 | 1/1992 | Dunklee | 206/363 |

Primary Examiner—Bryon P. Gehman
Attorney, Agent, or Firm—Emil Richard Skula

[57] ABSTRACT

A thermoformed blister package for a surgical instrument. The package has a tray having at least one cavity having at least one undercut and an instrument can be quickly released from a cavity and from the package without touching the instrument. The package also has an interlocking projection for efficiently storing packages in a dispenser container.

3 Claims, 8 Drawing Sheets

QUICK RELEASE PACKAGE FOR SURGICAL INSTRUMENT

This is a continuation, of application Ser. No. 08/162,687, filed Dec. 6, 1993, now abandoned.

TECHNICAL FIELD

The field of art to which this invention relates is packaging, in particular packaging for endoscopic instruments.

BACKGROUND OF THE INVENTION

The use of thermoformed blister packages for packaging surgical and endoscopic surgical ("endosurgical") instruments is well-known in the art. The thermoformed blister packages typically have a plurality of cavities formed therein for receiving and retaining a particular surgical instrument. The cavities are typically designed to conform to each section of the surgical instrument; for example, in the case of a trocar, a large proximal cavity will receive the handle while a long distal cylindrical cavity will receive the trocar cannula tube and obturator. It is known that endosurgical instruments such as trocars typically have long shafts, which enable the surgeons to access a patient's body cavity. In order to retain the instrument in the thermoformed blister package and prevent it from moving during shipping, handling, storage, sterilization and the like, it is known to include undercuts in the blister tray. These undercuts are projections that extend over the top of the opening of a cavity in which all or part of an instrument is contained. The gap between the undercuts is typically less than the width of the opening of the cavity thereby serving to assist in preventing an instrument or part thereof from being released from the cavity.

Although the use of undercuts is effective in retaining an instrument in a cavity of a blister formed tray, there are also disadvantages associated with the use of undercuts. In particular, at the point of use in the operating room, it may be difficult for a scrub nurse to remove an instrument from a cavity of a blister package having undercuts in order place it in the sterile operating field. In order to remove an instrument from a cavity having undercuts, it is typically necessary to grasp the instrument with one hand while holding the package with the other hand. An upward force applied by the scrub nurse to the instrument causes the undercuts to rotate in opposite directions about the cavity, thereby having the effect of widening the gap between the uppercuts and allowing the instrument to be withdrawn from the cavity. The requirement of having to grasp the instrument for removal from a blister package is disadvantageous because it may compromise the sterility of the instrument and/or the sterile field of the operating room. Other disadvantages of existing packages include difficulty in removing an instrument efficiently and quickly from a blister package having cavities with undercuts and the need for additional packaging components required to retain the instrument in the package when undercuts are not used. It is also known that blister packages may not have efficient storage configurations, first of all, because of the rigid materials used that will not conform about the product exterior and, secondly, because allowances must be made for high profile areas of the product in the package and hand hold areas to hold the package when dispensing the instrument. This often represents a problem since hospital storage areas typically have limited storage space available.

Therefore, what is needed in this art is a package for an endoscopic instrument having a thermoformed blister tray with cavities having undercuts, which has a quick-release feature wherein it is not necessary to grasp the instrument to release it from the package, thereby possibly eliminating the need for a scrub nurse to be present to remove a sterile instrument and place the instrument into the sterile field during the initial set-up for a sterile procedure.

SUMMARY OF THE INVENTION

Accordingly, it is an object of the present invention to provide a thermoformed blister package for a surgical instrument which has a quick-release feature.

It is yet a further object of the present invention to provide a package wherein a sterile instrument may be quickly released from the package without touching the instrument and potentially compromising its sterility.

It is yet another object of the present invention to provide a package for an endoscopic instrument which conserves packaging and shelf space by having an interlocking projection.

Accordingly, a thermoformed blister package for a surgical instrument is disclosed. The thermoformed blister package comprises a tray having an outwardly extending flange. At least one cavity is formed in said tray for receiving a surgical instrument. At least one undercut extends over at least one cavity for retaining the instrument in the cavity. The tray has means for quickly releasing the instrument from the tray. The release means preferably comprises two finger pads. The finger pads are located a sufficient distance apart along the longitudinal axis of the package to effectively open up the undercut by flexing the package when the pads are pressed and the flanges are restrained, thereby releasing the instrument from the cavity.

Yet another aspect of the present invention is a thermoformed blister package having a cavity which extends substantially below the bottom of the package thereby forming an interlocking projection. The cavity is skewed toward either end of the package. This feature allows the packages to be efficiently stacked by interlocking the packages such that the interlocking projections are adjacent to each other.

Still yet another aspect of the present invention is the combination of a dispensing container and a plurality of the above-described packages stacked within the container in an interlocking manner.

Other features and advantages of the invention will become more apparent from the following description and accompanying drawings.

BEST MODE FOR CARRYING OUT THE INVENTION

Figure 8:
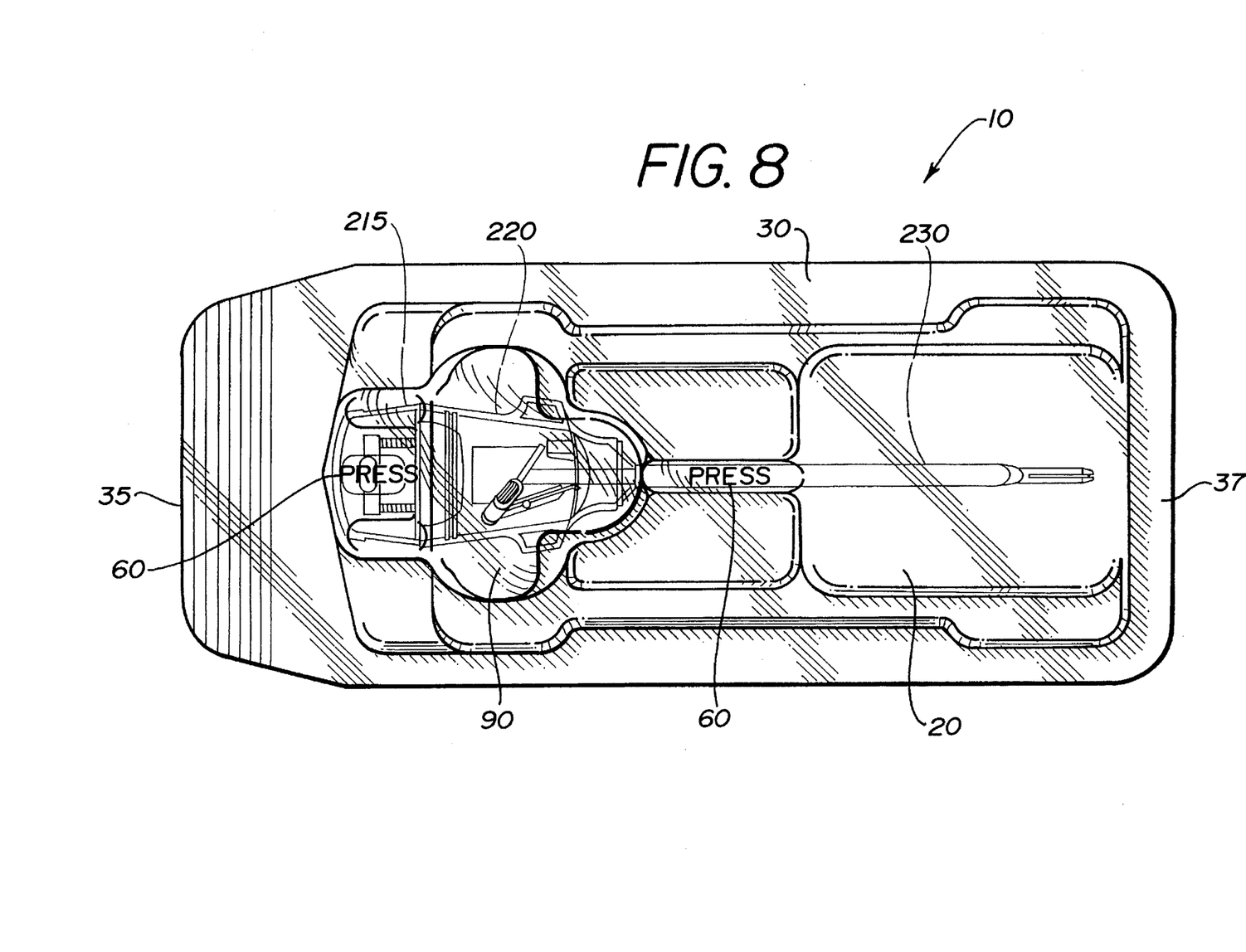
FIG. 8 is a bottom view of the package of FIG. 1 illustrating the finger pads 60 which are pressed to quickly release an instrument from the tray.

The package 10 of the present invention is illustrated in FIGS. 1–4. The package is seen to have thermoformed blister tray 20 and cover 100. Thermoformed blister tray 20 is seen to have outwardly extending flange 30 and cavity 40 for receiving the handle 210 of the trocar 200. The handle 210 consists of the trocar obturator handle 215 interlocked with the trocar cannula handle 220. Cavity 40 projects downwardly a sufficient distance to effectively form interlocking projection 90. Interlocking projection 90 is seen to project downwardly from the bottom of tray 20 and is also seen to be skewed toward an end of the tray 20. The tray 20 is also seen to have the longitudinal cylindrical cavity 50 for receiving the cannula tube 230 of the trocar 200. The cavity 50 is seen to have top extending opposed undercut projections 55 for retaining the shaft 230 in the cavity 50 during shipping, handling, sterilization, storage, etc. A gap 58 between the undercut projections 55 is sufficiently narrow to prevent the shaft 230 from dislodging from cavity 50. The flange 30 is seen to have an outwardly extending end section 35, having a gripping surface 36 and opposed end section 37. Referring to FIG. 8, the bottom of the tray 20 is seen to have two finger pads 60. The cavities formed in the tray 20 of package 10 may be shaped to accommodate various surgical instruments, although it is preferred to use the package 10 to package trocars and other endoscopic instruments having elongated shafts or members. The ease of undercuts on the cavities will vary in accordance with the shape, size, weight, etc., of the instrument.

Figure 9:
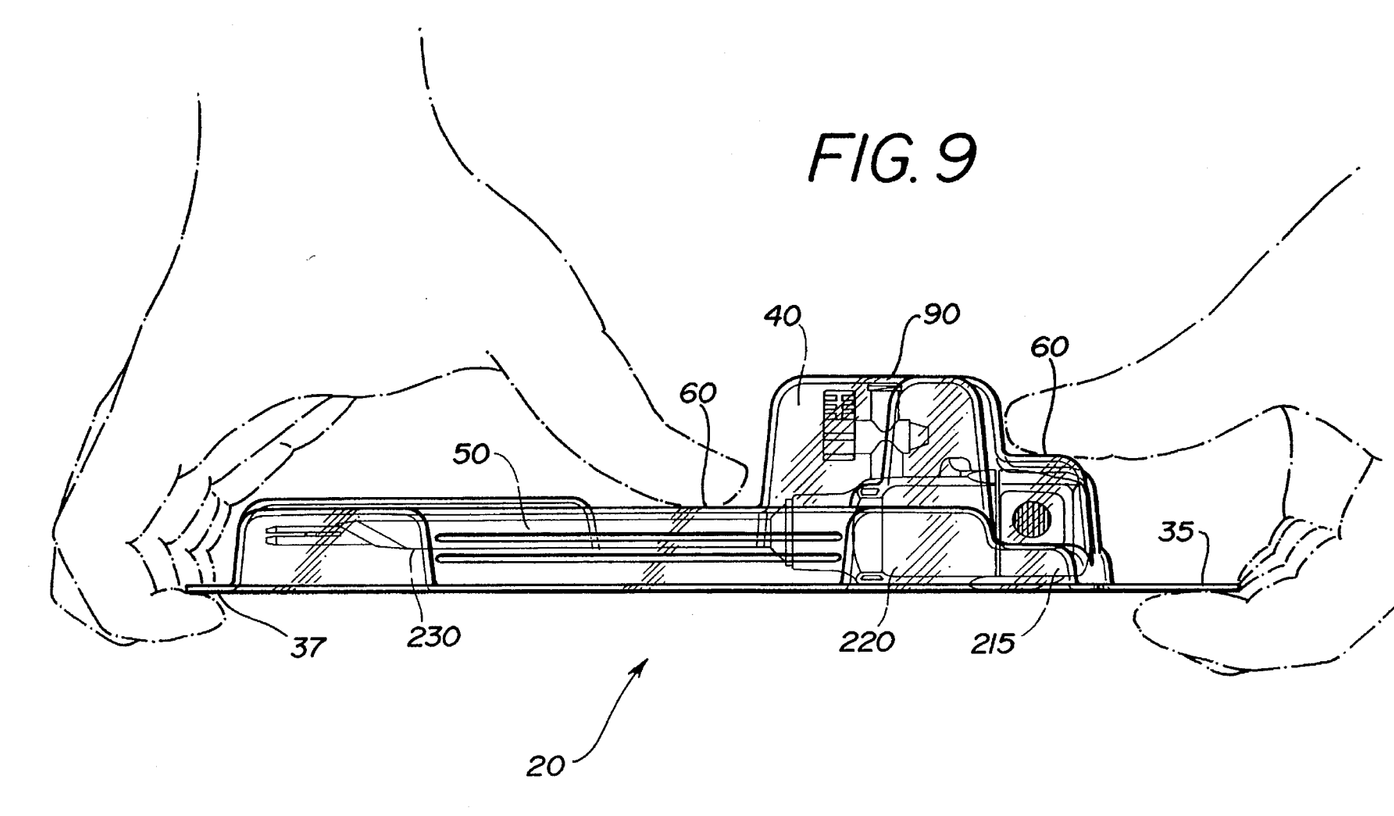
FIG. 9 is a side view of the package of FIG. 1 after the cover has been removed illustrating the user's thumbs pressing the bottom finger pads while the user's remaining fingers press along the top of the end sections of the flange of the tray.
Figure 10:
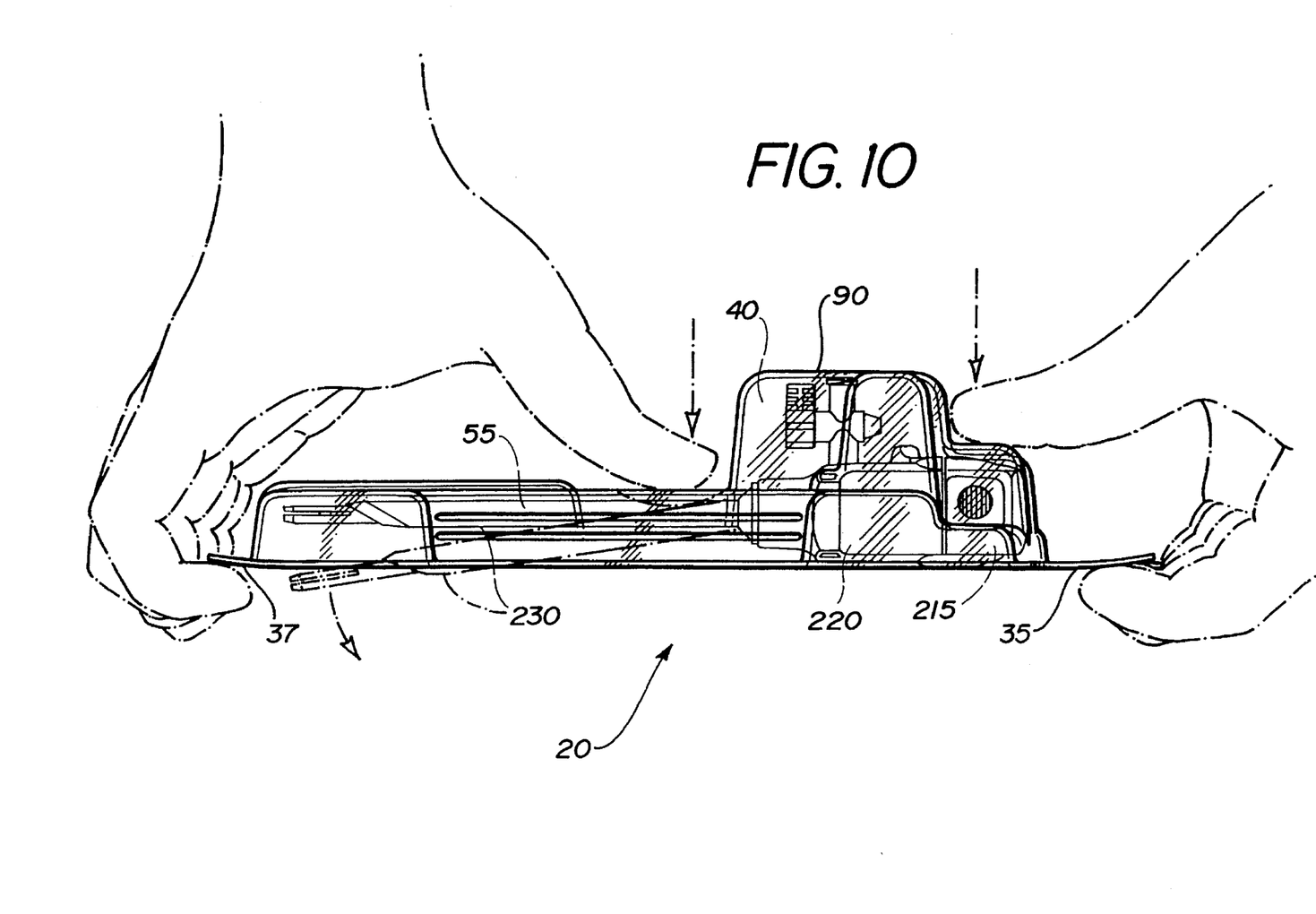
FIG. 10 illustrates a side view of the package of FIG. 9 after the gap between the undercuts of the cavity containing the trocar cannula tube has been opened sufficiently to allow the cannula to fall free from both the cavity and the tray.

As seen in FIG. 8, the finger pads 60 are formed into the bottom of the tray 20. Referring also to FIGS. 9 and 10, the pads 60 are seen to be sufficiently spaced along the longitudinal axis of tray 20 such that pressing pads 60 with the thumbs of both hands while engaging the top of flange 30 with the remaining fingers of the hands along end section 35 and end section 37, respectively, causes the undercuts 55 to rotate outwardly. This causes the gap 58 to increase sufficiently to effectively allow trocar cannula tube 230 to be released from the cavity 50. The trocar 200 is then released and free to fall from the tray 20, e.g., into a sterile field, without having to manually grasp or manipulate the trocar. The lid 100 is seen to be a generally rectangularly shaped member, having an angulated end 105 corresponding to end flange section 35.

Figure 1:
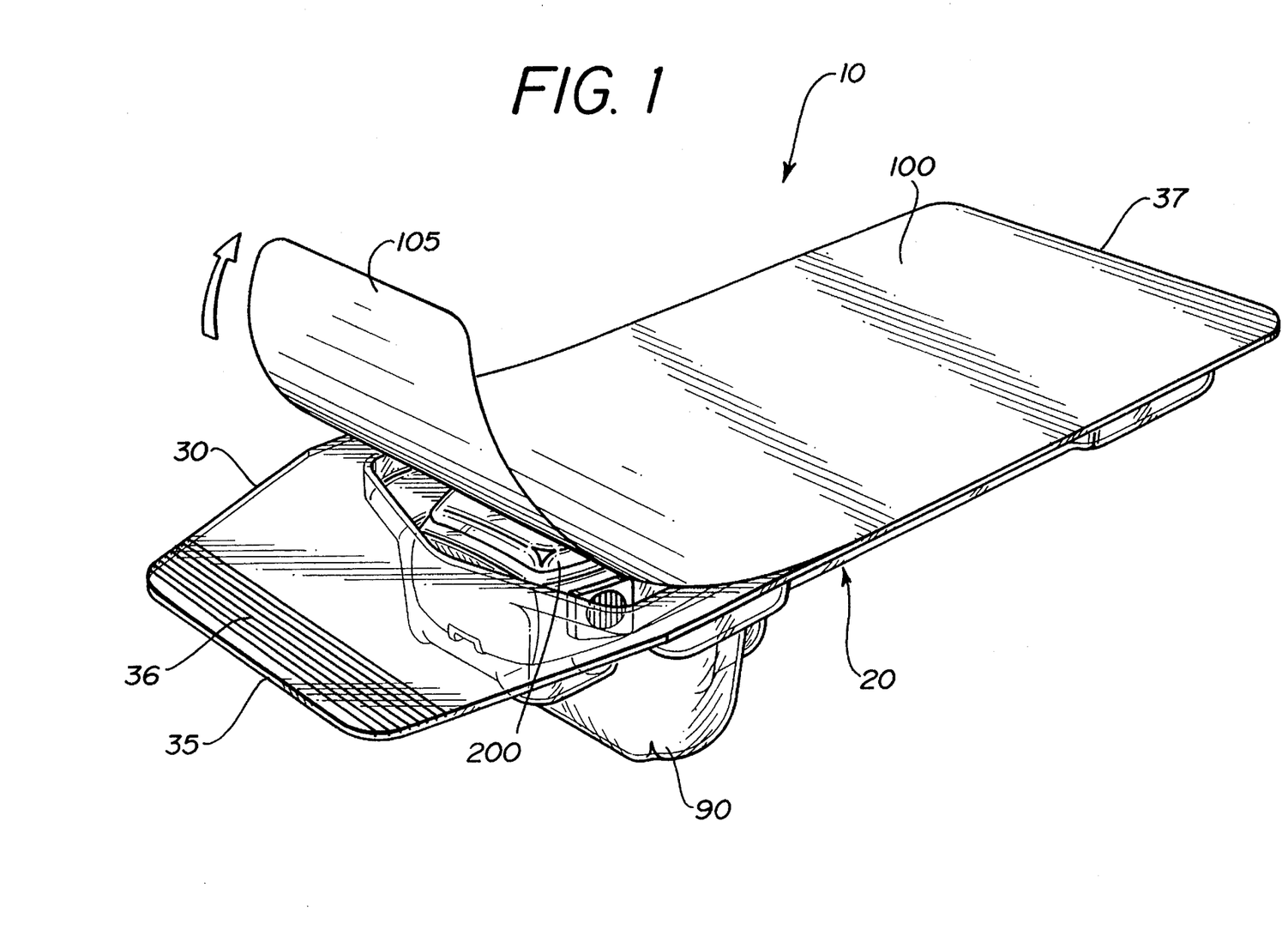
FIG. 1 is a perspective view of a package of the present invention containing a trocar wherein the lid of the package is shown in a partially peeled-open position.
Figure 2:
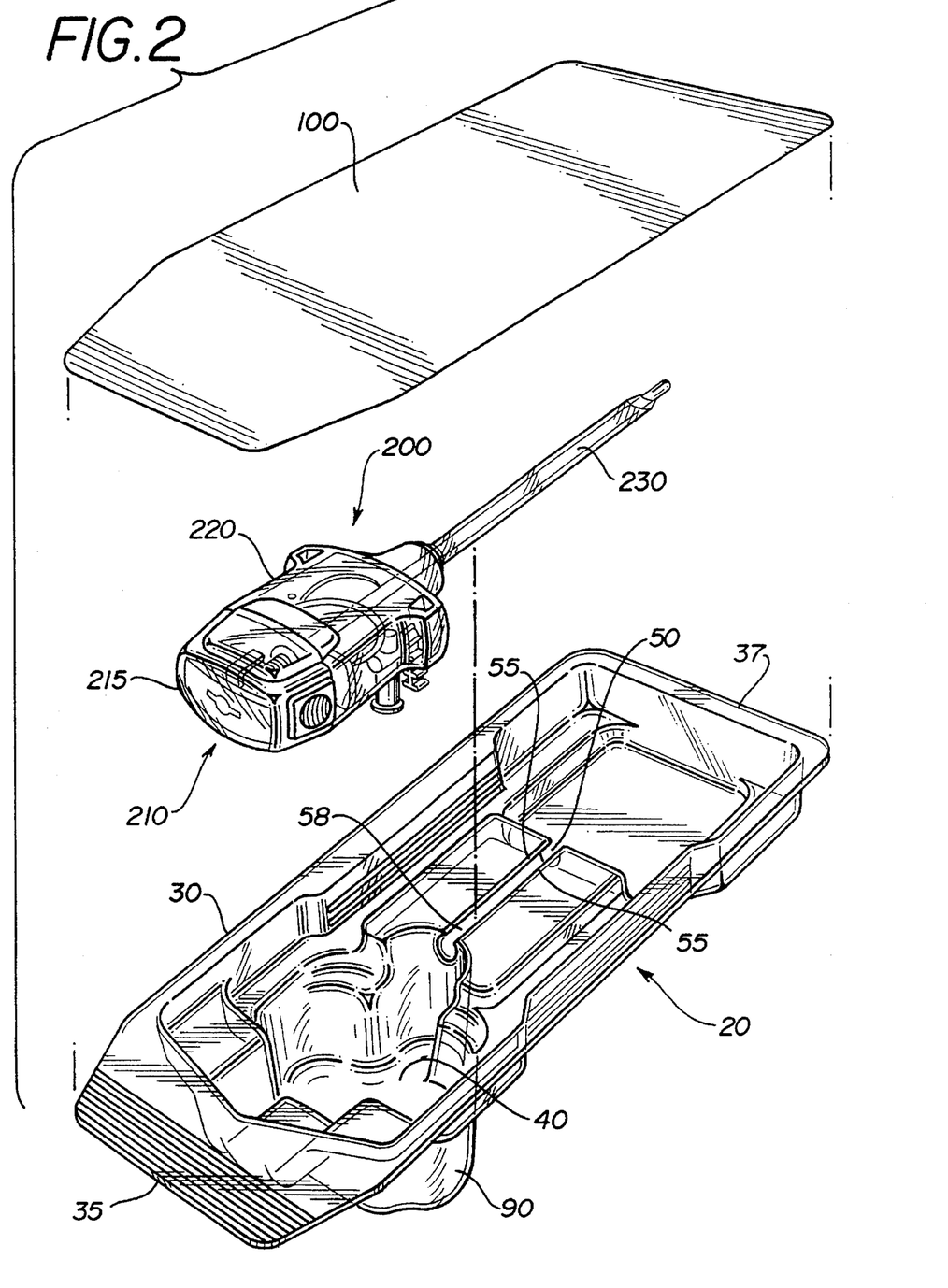
FIG. 2 is an exploded perspective view of the package of the present invention showing a blister tray, a trocar and a cover.
Figure 3:
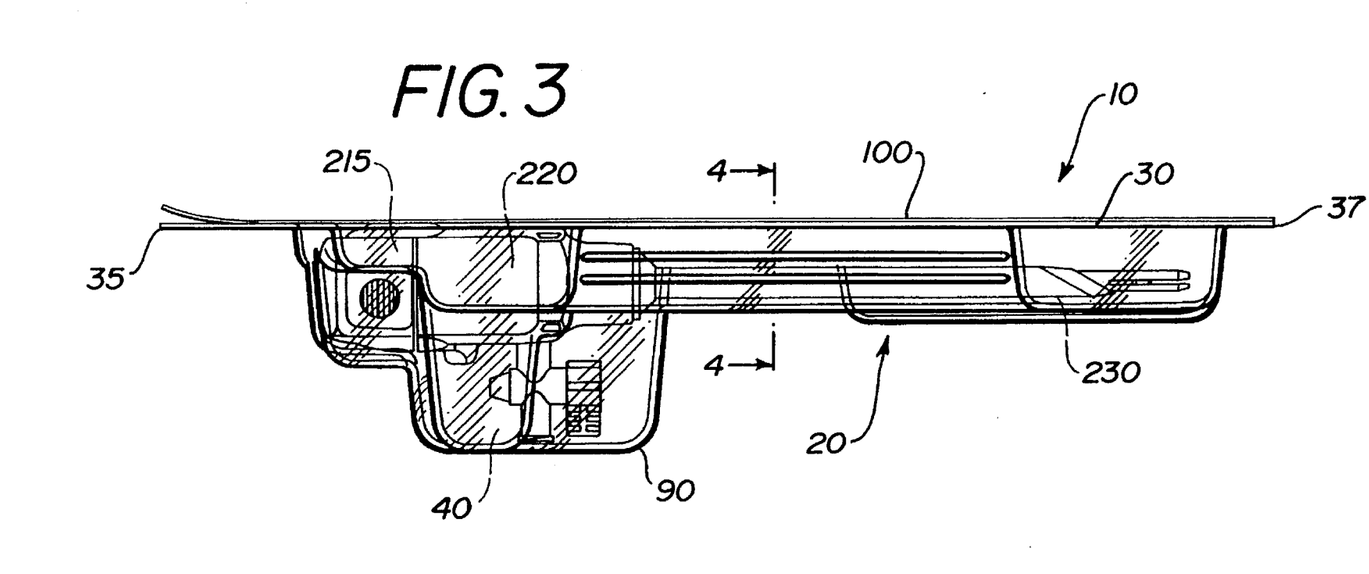
FIG. 3 is a side view of a sealed package of the present invention containing a conventional trocar; the interlocking projection is illustrated.
Figure 4:
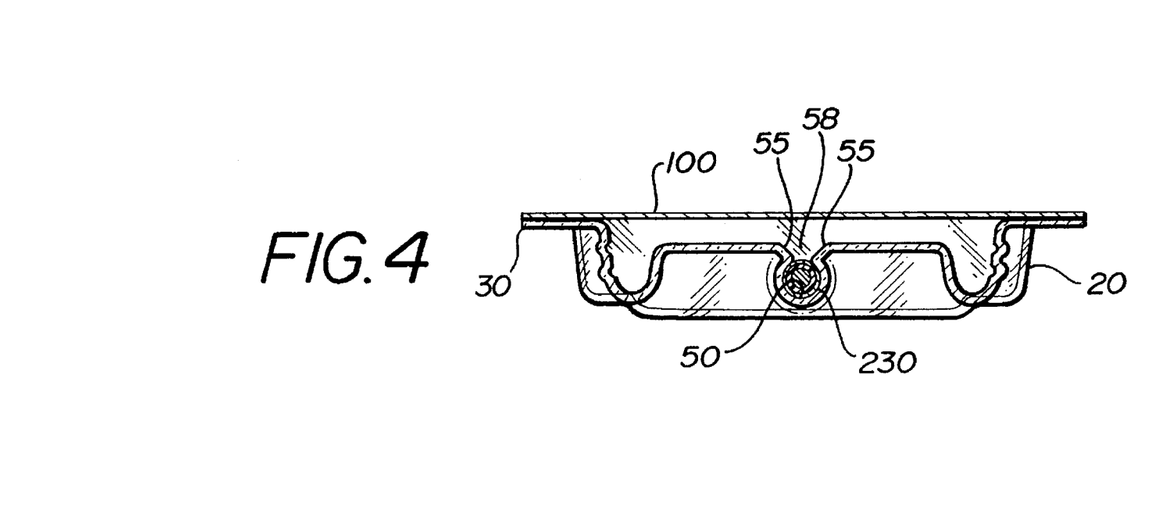
FIG. 4 is a cross-sectional of the package of FIG. 3 taken along View Line 4—4 showing the shaft of the trocar in a cavity having undercuts.
Figure 5:
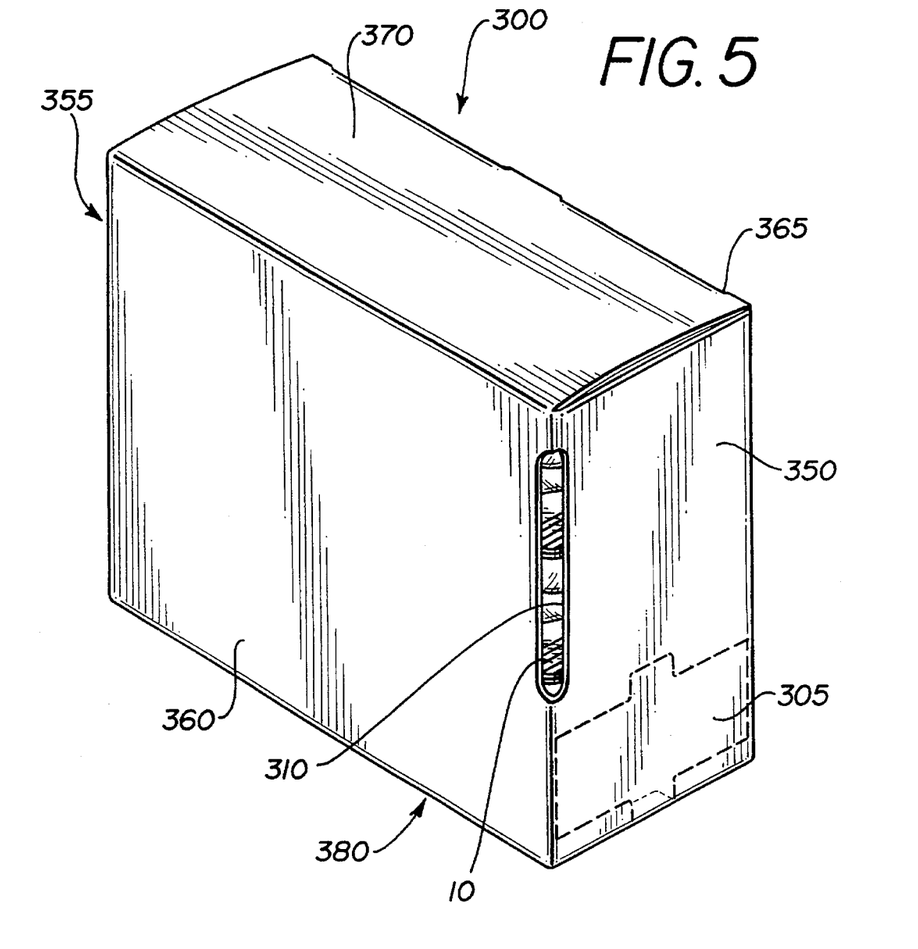
FIG. 5 illustrates a perspective view of a dispensing container for packaging the packages of the present invention wherein the packages are stacked in an interlocking configuration.
Figure 6:
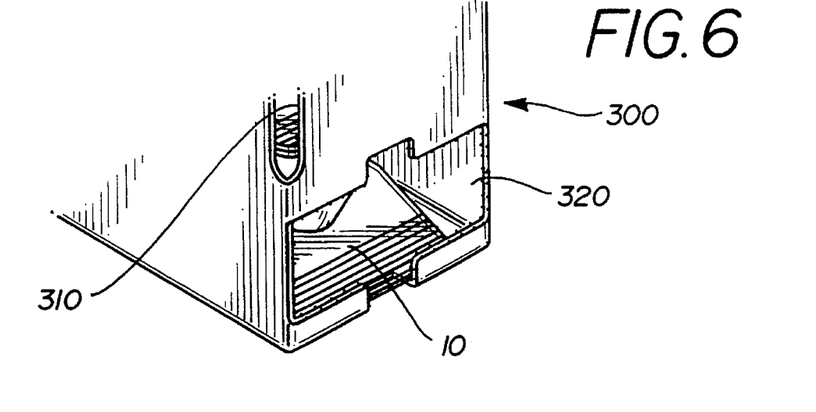
FIG. 6 is a partial perspective view of a dispensing opening of the container of FIG. 5 illustrating a bottom dispensing opening and a slot for viewing the interior of the container.
Figure 7:
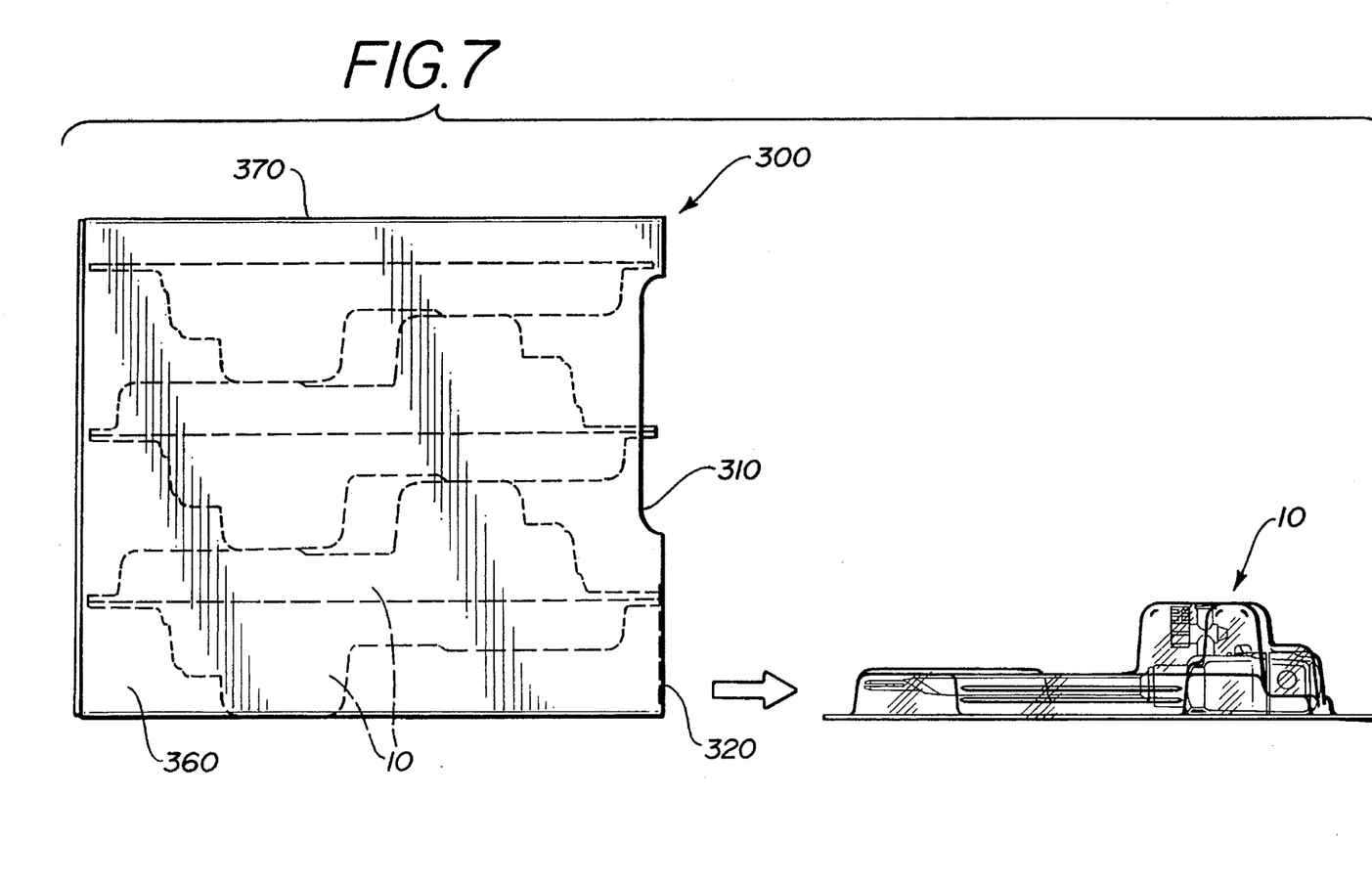
FIG. 7 is a side view of the dispensing container of FIG. 5 showing in phantom packages of the present invention contained therein in an interlocking configuration;a package of the present invention is seen as it is dispensed from the container dispensing opening; the packages are seen to have interlocking projections.

Referring to FIGS. 5, 6 and 7, an outer dispensing container 300 for the packages 10 of the present invention is seen. The dispensing container 300 consists of opposed front and back walls 350 and 355, respectively, opposed connecting side walls 360 and 365, and top wall 370 and bottom wall 380. The walls are preferably connected as necessary along conventional fold lines or perforations. The package is seen to have a lower end perforated portion 305 formed by score line 306, which is removable to form dispensing outlet 320 from which the interlocked stacked packages 10 are removed. Vertical vent 310 contained in the corner of package of 300 allows the user to determine the number of packages 10 remaining in the outer container 300. Referring to FIG. 7, the interlocking configuration of the packages 10 within the outer container 300 is seen. The packages 10 are packed in the outer container 300 in a manner wherein the bottoms of adjoining packages 10 face each other such that interlocking projections 90 of packages 10 are adjacent to each other. Thus, the use of interlocking storage packages 10 in the outer dispensing container 300 conserves space by allowing more packages 10 to be stored in a container than conventional packages not having this interlocking feature.

The thermoformed blister packages of the present invention are formed using conventional thermoforming equipment and conventional thermoforming processes. The thermoforming process typically consists of an initial stage wherein a sheet of plastic is heated to a sufficient temperature where it is effectively formable. Then, the heated plastic sheet is placed over a mold having cavities conforming to the structure of the package. Next, a vacuum is drawn through perforations in the mold to form the plastic into a configuration which conform to the contours of the mold. Next, the formed plastic sheet is cooled to a temperature below its moldable state, and the formed component is then removed from the mold.

The plastic sheeting, which can be used to manufacture the thermoformed blister trays 20 of the present invention for use in packaging medical devices, includes suitable, conventional plastic sheeting materials known in the art and equivalents such as polyethylene terephthlate(PETE), polyvinyl chloride (PVC), polypropylene(PP) and polystyrene(PS) and the like. It is particularly preferred, when manufacturing the packages 20 of the present invention to use polyethylene terephthalate. The thickness of the sheet material is typically as thin as possible but sufficiently thick to effectively provide sufficient mechanical strength. The thicknesses may, for example, vary from about 0.010 inches to about 0.060 inches.

The dispensing container 30 is made from any conventional packaging materials including fiber board, paper, plastics, composites and the like having sufficient rigidity to effectively function in a package. It is particularly preferred to use solid bleached sulphate board, clay coated newsback, clay coated kraft and the like.

The cover 100 used in the package 10 can be made from coated or uncoated Tyvek®, coated paper, non-porous plastic film and the like. The cover 100 is sealed to the flange 30 using conventional sealing techniques including heat sealing, pressure sealing, RF sealing, impulse sealing, ultrasonic sealing and the like and combinations thereof.

The sealed package 10 containing a trocar 200 or other medical device is sterilized using conventional sterilization processes and cycles. The package 10 may be sterilized using gaseous sterilants including ethylene oxide as well as radiation. The trocar 200 may also be aseptically packaged package 10.

There are numerous advantages associated with the packages 10 of the present invention. It is now possible to utilize a thermoformed blister tray for a surgical instrument which has a quick-release feature such that the instrument can be removed quickly and efficiently from the package without having to grasp the instrument by merely manipulating the exterior of the package. Another advantage of the packages 10 of the present invention is that when stacked in accordance with the previously-mentioned configuration in an outer container of the present invention, the shelf space required for storage of the packages is reduced.

Although this invention has been shown and described with respect to detailed embodiments thereof, it will be understood by those skilled in the art that various changes in form and detail thereof may be made without departing from the spirit and scope of the claimed invention.

What is claimed is:

1. A thermoformed blister package, comprising:
    a tray having a top, a bottom and a center;
    a flange extending outwardly from the tray;
    a plurality of cavities in said tray for receiving a surgical instrument wherein each said cavity has a top opening and wherein at least one of the cavities has at least one undercut extending from the tray adjacent to the top of the at least one cavity for retaining at least a portion of a said instrument within the cavity, each undercut partially extending into the top opening of the cavity thereby forming a gap; and,
    means for quickly releasing a said instrument from the tray without touching the instrument wherein the means for quickly releasing the instrument from the tray comprises two finger pads extending from the bottom of the tray and spaced sufficiently apart to open up the gap sufficient to release the instrument when the pads are pressed while holding the outwardly extending flange.

2. The package of claim 1 wherein at least one cavity having the at least one undercut has a substantially circular cross-section.

3. The package of claim 1 wherein the bottom of the tray beneath one cavity in said tray extends downwardly to form an interlocking projection thereby dividing the bottom of the tray into an interlocking projection and an interlocking bottom section, wherein said projection is offset from the center of the tray such that the interlocking projection and interlocking bottom section of one package can interlock with the interlocking projection and interlocking bottom section of another package.

* * * * *